(12) United States Patent
Zoller et al.

(10) Patent No.: US 8,921,404 B2
(45) Date of Patent: Dec. 30, 2014

(54) AZOLE DERIVATIVES IN THE FORM OF LIPASE AND PHOSPHOLIPASE INHIBITORS

(75) Inventors: Gerhard Zoller, Frankfurt am Main (DE); Stefan Petry, Frankfurt am Main (DE); Gunter Muller, Frankfurt am Main (DE); Hubert Heuer, Frankfurt am Main (DE); Norbert Tennagels, Frankfurt am Main (DE)

(73) Assignee: Sanofi, Paris (FR)

( * ) Notice: Subject to any disclaimer, the term of this patent is extended or adjusted under 35 U.S.C. 154(b) by 1740 days.

(21) Appl. No.: 11/873,846

(22) Filed: Oct. 17, 2007

(65) Prior Publication Data

US 2008/0090867 A1   Apr. 17, 2008

Related U.S. Application Data

(63) Continuation of application No. PCT/EP2006/003411, filed on Apr. 13, 2006.

(30) Foreign Application Priority Data

Apr. 20, 2005 (DE) .......................... 10 2005 018 389

(51) Int. Cl.
| | |
|---|---|
| *A61K 31/4523* | (2006.01) |
| *A61K 31/423* | (2006.01) |
| *A61K 31/428* | (2006.01) |
| *C07D 275/04* | (2006.01) |
| *C07D 498/04* | (2006.01) |
| *C07D 261/20* | (2006.01) |
| *C07D 413/12* | (2006.01) |
| *C07D 513/04* | (2006.01) |

(52) U.S. Cl.
CPC ............ *C07D 261/20* (2013.01); *C07D 275/04* (2013.01); *C07D 413/12* (2013.01); *C07D 513/04* (2013.01)
USPC ........... 514/379; 514/373; 514/397; 548/241; 548/207; 546/198

(58) Field of Classification Search
CPC ............ A61K 31/4523; A61K 31/423; A61K 31/428; C07D 275/04; C07D 498/04
USPC ........... 548/241, 207; 546/198; 514/373, 397, 514/379
See application file for complete search history.

(56) References Cited

U.S. PATENT DOCUMENTS

| 6,683,080 B2 * | 1/2004 | Fryburg et al. ............... 514/242 |
| 2003/0011420 A1 | 1/2003 | Salvati et al. |
| 2007/0197610 A1 * | 8/2007 | Kennis et al. ................. 514/365 |

FOREIGN PATENT DOCUMENTS

| WO | WO 03/051842 | 6/2003 |
| WO | WO 2004/094393 | 11/2004 |
| WO | WO 2004/094394 | 11/2004 |
| WO | WO 2006/054652 | 5/2006 |

OTHER PUBLICATIONS

Ricci, "Cytokinin-like activity of N'-substituted N-phenylureas", Plant Growth Regulation, Plant Growth Regulation, 2001, 34, 167-172.*

Vicini, "Synthesis and phytotoxic activity of benzene-substituted 1,2-benzisothiazol-3-ylureas", Farmaco, Edizione Scientifica (1986), 41(10), 808-18.*

* cited by examiner

*Primary Examiner* — Sreeni Padmanabhan
*Assistant Examiner* — Sahar Javanmard
(74) *Attorney, Agent, or Firm* — Scully, Scott, Murphy & Presser, P.C.

(57) ABSTRACT

The invention relates to azole derivatives of the general formula I

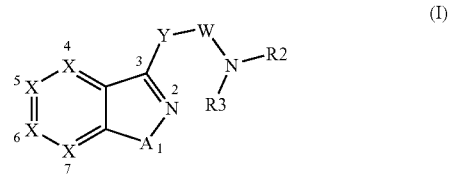

as defined in the present application as well as to their uses in treatment of conditions that would benefit from their inhibitory effect on hormone sensitive lipase, HSL, an allosteric enzyme in adipocytes which is inhibited by insulin and is responsible for the breakdown of fats in fat cells and thus for transferring fat constituents into the blood stream. Inhibition of this enzyme is therefore equivalent to an insulin-like effect of the compounds of the invention.

7 Claims, No Drawings

AZOLE DERIVATIVES IN THE FORM OF LIPASE AND PHOSPHOLIPASE INHIBITORS

FIELD OF THE INVENTION

The present invention relates to azole derivatives of the general formula I, to the pharmaceutically usable salts thereof and to the use thereof as medicinal substances.

BACKGROUND OF THE INVENTION

WO 2003/0051842 A2 describes compounds for inhibiting hormone-sensitive lipase. These include benzisoxazole derivatives and benzisothiazole derivatives. Benzisoxazole derivatives for inhibiting glycogen synthase kinase 3 are described in WO 2004/058749.

It is an object of the present invention to provide alternative compounds which have an inhibitory effect on hormone-sensitive lipase or endothelial lipase.

DETAILED DESCRIPTION

The invention relates to azole derivatives of the general formula I wherein the meanings are:
A is selected from S and O;
W is selected from —(C═O)—, —(S═O)— and —(SO$_2$)—;
X is independently selected from ═C(—R)— and ═N—;
Y is —O— or —NR1-;
R is selected from hydrogen, halogen, (C$_1$-C$_6$)-alkyl, (C$_1$-C$_3$)-alkyloxy-(C$_1$-C$_3$)-alkylene, hydroxy, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, COOR4, trifluoromethyl, (C$_1$-C$_6$)-alkylsulfonyl, (C$_1$-C$_6$)-alkylsulfinyl, aminosulfonyl, nitro, pentafluorosulfanyl, (C$_6$-C$_{10}$)-aryl, CO—NR2R3, O—CO—NR2R3, O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—NR2R3 and unsubstituted or mono- or poly-F-substituted (C$_1$-C$_6$)-alkyloxy;
R1 is selected from hydrogen, (C$_1$-C$_6$)-alkyl, and benzyl;
R2 is selected from (C$_5$-C$_{16}$)-alkyl, and (C$_1$-C$_4$)-alkyl-(C$_6$-C$_{10}$)-aryl, wherein aryl may optionally be substituted one or more times by a substituent selected from halogen, (C$_1$-C$_6$)-alkyl, (C$_1$-C$_3$)-alkyloxy, hydroxy, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, (C$_1$-C$_6$)-alkoxycarbonyl, cyano, trifluoromethyl, trifluoromethyloxy, (C$_1$-C$_6$)-alkylsulfonyl, aminosulfonyl, and nitro;
R3 is hydrogen, or (C$_1$-C$_6$)-alkyl; or
R2 and R3 taken together with the nitrogen atom to which they are bonded, may form a monocyclic saturated or partially unsaturated 4- to 7-membered ring system or a bicyclic saturated or partially unsaturated 8- to 14-membered ring system, wherein individual members of the ring systems may be replaced by one to three atoms or atomic groups selected from the group —CHR5-, —CR5R5-, —(C═R5)-, —NR5-, —C(═O)—, —O—, —S—, —SO—, —SO$_2$—, with the proviso that no two units from the group —O—, —S—, —SO—, —SO$_2$— may be adjacent;
R4 is hydrogen, (C$_1$-C$_6$)-alkyl, or benzyl;
R5 is selected from (C$_1$-C$_6$)-alkyl, halogen, trifluoromethyl, COOR4, cyclopropyl, cyclopropylene; and
the tautomeric forms of the compounds and the physiologically tolerated salts thereof.

Preferred compounds of the formula I are those in which
W is —(C═O)—.

Further preferred compounds of the formula I are those in which
W is —(C═O)—;
X is independently selected from ═C(—R)— and ═N—;
Y is —O—, or —NR1-;
R is hydrogen, halogen, (C$_1$-C$_6$)-alkyl, hydroxy, amino, COOR4, trifluoromethyl, (C$_1$-C$_6$)-alkylsulfonyl, nitro, pentafluorosulfanyl, (C$_6$-C$_{10}$)-aryl, CO—NR2R3, O—CO—NR2R3 or O—CO—(C$_1$-C$_6$)-alkylene-CO—O—(C$_1$-C$_6$)-alkyl;
R1 is hydrogen, or (C$_1$-C$_6$)-alkyl;
R2 is (C$_6$-C$_{10}$)-alkyl, or (C$_1$-C$_3$)-alkyl-(C$_6$-C$_{10}$)-aryl, wherein the aryl may optionally be substituted one or more times by a substituent selected from halogen, (C$_1$-C$_6$)-alkyl, (C$_1$-C$_3$)-alkyloxy, hydroxy, amino, (C$_1$-C$_6$)-alkylamino, trifluoromethyl, and nitro;
R3 is hydrogen, or (C$_1$-C$_6$)-alkyl; or
R2 and R3 together with the nitrogen atom to which they are bonded, may form a monocyclic, saturated 5- to 6-membered ring system or a bicyclic saturated or partially unsaturated 9- to 10-membered ring system, wherein individual members of the ring systems may be replaced by one to three atoms or atomic groups selected from the series —CHR5-, —CR5R5-, —(C═R5)-, —NR5-, —O—, —S—, with the proviso that two units from the series —O—, —S— may not be adjacent;
R4 is hydrogen, (C$_1$-C$_6$)-alkyl, or benzyl; and
R5 is (C$_1$-C$_6$)-alkyl, halogen, trifluoromethyl, COOR4, cyclopropyl, or cyclopropylene.

Other preferred compounds of formula I are those in which
W is —(C═O)—;
X is independently ═C(—R)— or ═N—;
Y is —O—, or —NR1-;
R is selected from hydrogen, halogen, (C$_1$-C$_6$)-alkyl, hydroxy, amino, COOR4, trifluoromethyl, (C$_1$-C$_6$)-alkylsulfonyl, nitro, pentafluorosulfanyl, (C$_6$-C$_{10}$)-aryl, CO—NR2R3, O—CO—NR2R3 or O—CO—(C$_1$-C$_6$)-alkylene-CO—O—(C$_1$-C$_6$)-alkyl, and (C$_1$-C$_6$)-alkyloxy;
R1 is hydrogen, or (C$_1$-C$_6$)-alkyl;
R2 is (C$_6$-C$_{10}$)-alkyl, or (C$_1$-C$_3$)-alkyl-(C$_6$-C$_{10}$)-aryl, wherein aryl may optionally be substituted one or more times by a substituent selected from halogen, (C$_1$-C$_6$)-alkyl, (C$_1$-C$_3$)-alkyloxy, hydroxy, amino, (C$_1$-C$_6$)-alkylamino, trifluoromethyl, and nitro;
R3 is hydrogen, or (C$_1$-C$_6$)-alkyl; or
R2 and R3 together with the nitrogen atom to which they are bonded, may form a monocyclic, saturated 5- to 6-membered ring system or a bicyclic saturated or partially unsaturated 9- to 10-membered ring system, whose individual members of the ring systems may be replaced by one to three atoms or atomic groups selected from the series —CHR5-, —CR5R5-, —(C═R5)-, —NR5-, —O—, and —S—, with the proviso that no two units from the series —O—, —S— may be adjacent;

R4 is hydrogen, $(C_1-C_6)$-alkyl, or benzyl; and
R5 is $(C_1-C_6)$-alkyl, halogen, trifluoromethyl, COOR4, cyclopropyl, or cyclopropylene.

Particularly preferred compounds of formula I are those in which
W is —(C=O)—;
X is independently selected from =C(—R)— and =N—;
Y is —O—;
R is hydrogen, halogen, nitro, hydroxy or $(C_1-C_6)$-alkyl;
R2 is $(C_6-C_{10})$-alkyl or benzyl, wherein benzyl may optionally be substituted by a substituent selected from halogen, $(C_1-C_6)$-alkyl and trifluoromethyl;
R3 is hydrogen, or $(C_1-C_6)$-alkyl; or
R2 and R3 together with the nitrogen atom to which they are bonded, may form a monocyclic, saturated 5- to 6-membered ring system, wherein individual members of the ring systems may be replaced by one to two atoms or atomic groups selected from the series —CHR5—, —NR5—; and
R5 is $(C_1-C_6)$-alkyl, or cyclopropyl.

A further particularly preferred embodiment are compounds of the formula I in which
W is —(C=O)—;
X is identically or differently =C(—R)— or =N—;
Y is —O—;
R is hydrogen, halogen, nitro, hydroxy, $(C_1-C_3)$-alkyloxy or $(C_1-C_6)$-alkyl;
R2 is $(C_6-C_{10})$-alkyl or benzyl, where benzyl may optionally be substituted by halogen, $(C_1-C_6)$-alkyl or trifluoromethyl;
R3 is hydrogen; or
R2 and R3 together with the nitrogen atom bearing them may form a monocyclic, saturated 5- to 6-membered ring system, whose individual members of the ring systems may be replaced by one to two atoms or atomic groups from the series —CHR5—, —NR5—; and
R5 is $(C_1-C_6)$-alkyl, trifluoromethyl or cyclopropyl.

Another particularly preferred embodiment is compounds of formula I in which
W is —(C=O)—;
X is independently =C(—R)— or =N—;
Y is —NR1-;
R is hydrogen, halogen, nitro, hydroxy or $(C_1-C_6)$-alkyl;
R1 is hydrogen, or $(C_1-C_6)$-alkyl;
R2 is $(C_6-C_{10})$-alkyl or benzyl, wherein the benzyl may optionally be substituted by halogen, $(C_1-C_6)$-alkyl or trifluoromethyl;
R3 is hydrogen, or $(C_1-C_6)$-alkyl; or, alternatively,
R2 and R3 together with the nitrogen atom to which they are bonded, may form a monocyclic, saturated 5- to 6-membered ring system, wherein individual members of the ring systems may be replaced by one to two atoms or atomic groups selected from —CHR5—, and —NR5—; and
R5 is $(C_1-C_6)$-alkyl, or cyclopropyl.

A further particularly preferred embodiment is compounds of the formula I in which
W is —(C=O)—;
X is independently =C(—R)— or =N—;
Y is —NR1-;
R is hydrogen, halogen, nitro, hydroxy, $(C_1-C_3)$-alkyloxy or $(C_1-C_6)$-alkyl;
R1 is hydrogen, or $(C_1-C_6)$-alkyl;
R2 is $(C_6-C_{10})$-alkyl or benzyl, wherein the benzyl may optionally be substituted by halogen, $(C_1-C_6)$-alkyl or trifluoromethyl;
R3 is hydrogen; or, alternatively,
R2 and R3 together with the nitrogen atom to which they are bonded, may form a monocyclic, saturated 5- to 6-membered ring system, wherein individual members of the ring systems may be replaced by one or two atoms or atomic groups from the series —CHR5—, —NR5—; and
R5 is $(C_1-C_6)$-alkyl, trifluoromethyl or cyclopropyl.

In one preferred embodiment of the invention, A in the compounds of formula I has the meaning O.

In another preferred embodiment of the invention, A in the compounds of the formula I has the meaning S.

In a further embodiment of the invention, Y in the compounds of formula I has the meaning O.

In a further embodiment of the invention, Y in the compounds of formula I has the meaning NR1, where R1 may have the abovementioned meanings.

Very particularly preferred compounds of formula I are those in which
NR2R3 is piperidine which contains CHR5 in position 4.

Further preferred compounds of formula I are those in which
X is independently =C(—R)—.

Further preferred compounds of formula I are those in which
X is independently =C(—R)— or =N—, with the proviso that exactly one X is equal to =N—.

Preferred compounds of formula I are also those in which
X in position 4, 5 and 6 is independently =C(—R)—, and in position 7 is =N—.

Further preferred compounds of formula I are those in which
X in position 4, 5 and 7 is =C(—R)— with R=hydrogen, and in position 6 R is not hydrogen.

Further preferred compounds of formula I are those in which
X in position 4 and 5 is =C(—R)— with R=hydrogen, and in position 6 R is not hydrogen.

The invention relates to compounds of formula I in the form of their salts, racemates, racemic mixtures and pure enantiomers, and to their diastereomers and mixtures thereof.

The alkyl radicals in the substituents R, R1, R2, R3, R4, R5 may be either straight-chain or branched. Halogen is fluorine, chlorine, bromine or iodine, in particular fluorine or chlorine.

Aryl means an aromatic carbocyclic mono- or bicyclic ring system which comprises 6 to 10 atoms in the ring or in the rings.

Heteroaryl is a mono- or bicyclic aromatic ring system having 5 to 12 ring members, in which at least one atom in the ring system is a heteroatom selected from the series N, O and S.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention, of formula I, for example an ester, which on administration to a mammal such as, for example, a human is able to form (directly or indirectly) a compound of formula I or an active metabolite thereof.

Physiologically functional derivatives also include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

The compounds of the invention of the general formula I have a surprising inhibitory effect on hormone sensitive lipase, HSL, an allosteric enzyme in adipocytes which is inhibited by insulin and is responsible for the breakdown of fats in fat cells and thus for transferring fat constituents into the blood stream. Inhibition of this enzyme is therefore equivalent to an insulin-like effect of the compounds of the invention, eventually leading to a reduction of free fatty acids in the blood and of blood glucose. They can therefore be employed for treating metabolic derangements such as, for example, for non-insulin-dependent diabetes mellitus, for diabetic syndrome and for direct pancreatic damage.

The compounds of the invention of the general formula I may additionally have an inhibitory effect on endothelial lipase (EL). The preferred substrate for EL is HDL, which has antiatherosclerotic activity. A reduction in the HDL level leads to progression of atherosclerosis and its sequelae such as metabolic syndrome and coronary heart disease. An inhibition of EL should thus lead to prevention of atherosclerotic disorders.

The compounds of the invention of the formula I may also have an inhibitory effect on triglyceride lipase.

It has further been found that the inhibitory effect of the compounds of the invention of the general formula I is selective in relation to other lipases.

Compounds of this type are particularly suitable for the treatment and/or prevention of:
1. Disorders of fatty acid metabolism and glucose utilization disorders
2. Disorders of the insulin sensitivity of myo-, adipo- and hepatocytes (insulin resistance)-metabolic syndrome.
3. Diabetes mellitus, especially type 2 diabetes, including the prevention of the sequelae associated therewith.
Particular aspects in this connection include
hyperglycemia,
improvement in insulin resistance,
improvement in glucose tolerance,
protection of the pancreatic β cells,
prevention of macro- and microvascular disorders.
4. Dyslipidemias and their sequelae such as, for example, atherosclerosis, coronary heart disease, cerebrovascular disorders etc, especially those (but not restricted thereto) which are characterized by one or more of the following factors:
high plasma triglyceride concentrations, high postprandial plasma triglyceride
concentrations,
low HDL cholesterol concentration
low ApoA lipoprotein concentrations
high LDL cholesterol concentrations
small dense LDL cholesterol particles
high ApoB lipoprotein concentrations
5. Various other conditions which may be associated with the metabolic syndrome, such as:
obesity (excess weight), including central obesity
thromboses, hypercoagulable and prothrombotic stages (arterial and venous)
high blood pressure
heart failure such as, for example (but not restricted thereto), following myocardial infarction, hypertensive heart disease or cardiomyopathy
6. Other disorders or conditions in which inflammatory reactions or cell differentiation may for example be involved are:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
pancreatitis
other inflammatory states
retinopathy
adipose cell tumors
adipose cell carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, lichen planus skin cancer such as, for example, basal-cell carcinomas, melanomas or cutaneous T-cell lymphomas localized benign epidermal tumors such as, for example, keratoderma, epidermal naevi chilblains high blood pressure syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2003. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S. The orally effective hypoglycemic active ingredients include, preferably, the sulfonylureas which act on the ATP-dependent potassium channel of the beta cells (e.g. disclosed in WO 97/26265 and WO 99/03861), biguanides, meglitinides, glucagon antagonists, oral GLP-1 agonists, DPP-IV inhibitors, insulin sensitizers, e.g. PPAR and PXR modulators and active ingredients such as, for example, oxadiazolidinediones, thiazolidinediones, inhibitors of liver enzymes which are involved in stimulating gluconeogenesis and/or glycogenolysis, modulators of glucose uptake such as, for example, glucosidase inhibitors, compounds which alter lipid metabolism and lead to a change in the blood lipid composition, compounds which reduce food intake or food uptake.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I are administered in combination with an active ingredient which acts on the ATP-dependent potassium channel of the beta cells, such as, for example, sulfonylureas (e.g. tolbutamide, glibenclamide, glipizide, glimepiride) or glinides (e.g. repaglinide).

In one embodiment, the compounds of the formula I are administered in combination with a biguanide such as, for example, metformin.

In one embodiment, the compounds of the formula I are administered in combination with a PPARgamma agonist or thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment, the compounds of the formula I are administered in combination with compounds with an inhibitory effect on SGLT-1 and/or 2, as disclosed directly or indirectly for example in WO2004/007517, WO2004/052902, WO2004/052903 and WO2005/121161.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol resorption inhibitor as described for example in WO 02/50027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6)). Caromax is a carob-containing product from Nutrinova, Nutrition Specialties & Food Ingredients GmbH, Industriepark Hoechst, 65926

Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (tesaglitazar, (S)-3-(4-[2-(4-methanesulfonyloxyphenyl)ethoxy]-phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the further active ingredient is one or more antidiabetics, hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients acting on the ATP-dependent potassium channel of the β cells, CART agonists, NPY agonists, MC4 agonists, orexin antagonists, H3 agonists, TNF agonists, CRF antagonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds of the invention of the formula I was tested in the following enzyme assay systems:

1. HSL Inhibition Assay 1.1. Preparation of the Partially Purified HSL:

Isolated rat fat cells are obtained from epididymal adipose tissue from untreated male rats (Wistar, 220-250 g) by collagenase treatment in accordance with published methods (e.g. S, Nilsson et al., Anal. Biochem. 158, 1986, 399-407; G. Fredrikson et al., J. Biol. Chem. 256, 1981, 6311-6320; H. Tornquist et al., J. Biol. Chem. 251, 1976, 813-819). The fat cells from 10 rats are washed three times by flotation with 50 ml of homogenization buffer (25 ml Tris/HCl, pH 7.4, 0.25 M sucrose, 1 mM ETDA, 1 mM DTT, 10 μg/ml leupeptin, 10 μg/ml antipain, 20 μg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.) and suspended in 2.5 ml of 20 mM Tris/HCl, pH 7.0, 1 mM EDTA, 65 mM NaCl, 13% sucrose, 1 mM DTT, 10 μg/ml leupeptin/pepstatin/antipain. The suspension is dialyzed against 25 mM Tris/HCl, pH 7.4, 50% glycerol, 1 mM DTT, 10 μg/ml leupeptin, pepstatin, antipain at 4° C. overnight and then loaded onto a hydroxyapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at −70° C. for 4 to 6 weeks.

1.2 HSL Activity Assay:

To prepare the substrate, 25-50 μCi of [3H]trioleoylglycerol (in toluene), 6.8 μmol of unlabeled trioleoylglycerol and 0.6 mg of phospholipids (phosphatidylcholine/phosphatidylinositol 3:1 w/v) are mixed, dried with $N_2$ and then taken up in 2 ml of 0.1 M KPi (pH 7.0) by ultrasound treatment (Branson 250, microtip, setting 1-2, 2×1 min with an interval of 1 min). After addition of 1 ml of KPi and renewed ultrasound treatment (4×30 sec on ice with intervals of 30 sec), 1 ml of 20% BSA (in KPi) is added (final concentration of trioleoylglycerol 1.7 mM). For the reaction, 100 μl of substrate solution are pipetted into 100 μl of HSL solution (HSL prepared as above, diluted in 20 mM KPi, pH 7.0, 1 mM EDTA, 1 mM DTT, 0.02% BSA, 20 μg/ml pepstatin, 10 μg/ml leupeptin) and incubated at 37° C. for 30 min. Addition of 3.25 ml of methanol/chloroform/heptane (10:9:7) and of 1.05 ml of 0.1 M $K_2CO_3$, 0.1 M boric acid (pH 10.5) is followed by thorough mixing and finally centrifugation (800×g, 20 min). After phase separation, one equivalent of the upper phase (1 ml) is removed and the radioactivity is determined by liquid scintillation measurement.

1.3 Evaluation of the HSL-Inhibitory Effect:

Substances are normally tested in four independent mixtures. The inhibition of the HSL enzymatic activity by a test substance is determined by comparing with an uninhibited control reaction. The $IC_{50}$ is calculated from an inhibition plot with at least 10 concentrations of the test substance. The GRAPHIT, Elsevier-BIOSOFT software package is used to analyze the data.

2. EL Inhibition Assay:

2.1. Preparation of EL

EL is released as secretory protein in high concentration into cell culture medium (conditioned medium) by recombinant cell lines (CHO, HEK293). This is employed as enzyme solution after concentration.

2.2. EL Activity Assay

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates the fluorescent dye Bodipy which can be detected after separation by thin-layer chromatography on an HPTLC plate (silica gel 60, Merck) or directly in the reaction vessel by measuring the fluorescence.

The substrate solution is prepared by taking up 100 μg of 1,2-bis(4,4-difluoro-5,7-dimethyl-4-bora-3a,4a-diaza-s-indacene-3-undecanoyl)-sn-glycero-3-phospho-choline (manufacturer Molecular Probes), 2.4 mg of tripalmitin (Sigma) and 7.9 mg of DOP—choline (1,2-dioleoyi-sn-glycero-3-phosphocholine) in 393 μl of chloroform and then transferring 157 μl into a fresh reaction vessel. After evaporation of the solvent, the lipid mixture is dissolved in 4 ml of 200 mM TRIS-HCl, 150 mM sodium chloride, pH=7.4, by sonication twice. The subsequent enzymic reaction takes place at 37° C. for 60 minutes. For this purpose, 45 μl of the substrate solution are incubated with 1 μl of inhibitor of appropriate concentration (dissolved in DMSO, pure DMSO solution is used as control) and 5 μl of enzyme solution (conditioned medium). Then 3 μl of the assay mixture are loaded onto an HPTLC plate (silica gel 60, Merck), and the liberated fluorescent dye is separated for detection with an eluent (diethyl ether:petroleum benzene:acetic acid [78:22:1]). After evaporation of the eluent, the plate is read in a fluorescence scanner. An increased release of the fluorescent dye in the uninhibited reaction is to be observed as a measure of the enzymic activity.

2.3. Evaluation of the EL-Inhibitory Effect:

The enzymatic activity is reduced as a function of the inhibitor concentration used, and the inhibitor concentration at which a half-maximum enzymatic activity is observed is called $IC_{50}$ In these assays, the compounds of the examples showed the following $IC_{50}$ values:

| Example | IC$_{50}$ [µM] HSL | IC$_{50}$ [µM] EL |
|---|---|---|
| 1 | 0.12 | |
| 2 | 0.12 | |
| 3 | 0.1 | |
| 4 | 0.1 | |
| 5 | 0.1 | |
| 7 | | 14.6 |
| 8 | | 14.6 |
| 10 | 0.67 | |
| 11 | 0.26 | |

Preparation Processes

The compounds of the invention of the general formula I are prepared by methods known per se, e.g. by acylation of substituted or unsubstituted azoles II with carbamoyl chlorides III (method A), or in two stages by reacting azoles II with phosgene or equivalents such as trichloromethyl chlorocarbonate, ditrichloromethyl carbonate or 4-nitrophenyl chloroformate and further reaction of the resulting azolecarboxylic acid derivative with amines IV (method B). For compounds in which R3 is hydrogen (formula Ia), the azoles II can also be reacted with the appropriate isocyanates V R2—N═C═O (method C).

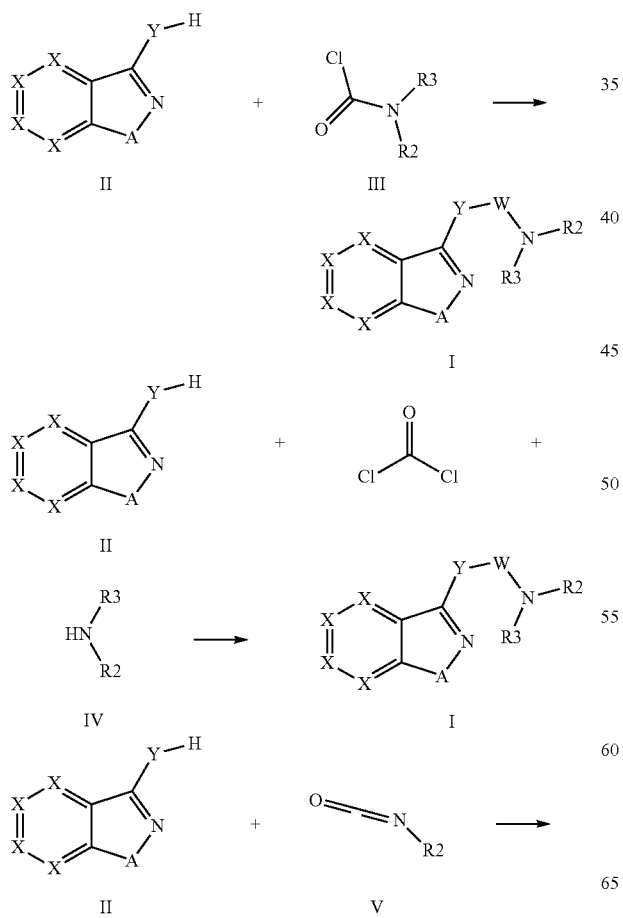

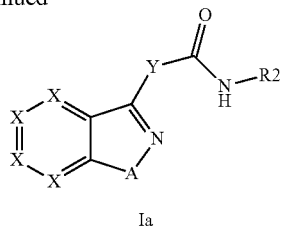

Ia

Since acids are usually liberated in these reactions, it is advisable to add bases such as pyridine, triethylamine, sodium hydroxide solution or alkali metal carbonates for expedition. The reactions can be carried out in wide temperature ranges. It has usually proved to be advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are used, strong bases such as lithium hydride, sodium hydride or potassium tert-butoxide in aprotic solvents such as THF or DMF have also proved suitable.

The azoles employed as starting compounds II, or corresponding aza-substituted derivatives, are commercially available or can be prepared by processes known from the literature (e.g. K. Bowden, G. Crank, W, J. Roos, J. Chem. Soc. 1968, 172-185; T. Chiyoda, K. Iida, K. Takatori, M. Kajiwara, Synlett 2000, 10, 1427-1428; M. A. Khan, F. K. Rafla, J. Chem. Soc. 1975, 693-694).

The examples detailed below serve to illustrate the invention without, however, restricting it.

EXAMPLES

Example 1

6-Chlorobenzo[d]isoxazol-3-yl 4-methylpiperidine-1-carboxylate 200 mg (1.18 mmol) of 6-chlorobenzo[d]isoxazol-3-ol, 228.7 mg (1.41 mmol) of 4-methylpiperidine-1-carbonyl chloride and 164 µl (2.36 mmol) of triethylamine were dissolved in 10 ml of pyridine and stirred at room temperature for 24 h. The reaction mixture was concentrated, and the residue was dissolved in water and extracted with ethyl acetate. The organic phase was concentrated and purified by preparative HPLC (PR18, acetonitrile/water 0.1% TFA). Yield: 147 mg (42%), M+H+: 295.2.

Example 2

Isoxazolo[5,4-b]pyridin-3-yl 4-methylpiperidine-1-carboxylate 125 mg (0.918 mmol) of isoxazolo[5,4-b]pyridin-3-ol, 178 mg (1.1 mmol) of 4-methylpiperidine-1-carbonyl chloride and 255 µl (1.84 mmol) of triethylamine were dissolved in 10 ml of pyridine and stirred at room temperature for 4 h. A further 89 mg (0.55 mmol) of 4-methylpiperidine-1-carbonyl chloride and 128 µl (0.92 mmol) of triethylamine were added, and stirring was continued at room temperature for 6 h. The reaction mixture was concentrated, and the residue was dissolved in water and extracted with ethyl acetate. The organic phase was concentrated and purified by preparative HPLC (PR18, acetonitrile/water 0.1% TFA). Yield: 101 mg (42%), M+H+: 262.1.

Example 3

6-Chlorobenzo[d]isoxazol-3-yl 4-trifluoromethylpiperidine-1-carboxylate

In analogy to example 1,200 mg (1.18 mmol) of 6-chlorobenzo[d]isoxazol-3-ol were reacted with 305 mg (1.41 mmol) of 4-trifluoromethylpiperidine-1-carbonyl chloride. Yield: 229 mg (56%), M+H+: 349.05.

Example 4

Isothiazolo[5,4-b]pyridin-3-yl 4-methylpiperidine-1-carboxylate

In analogy to example 1, 60 mg (0.4 mmol) of isothiazolo[5,4-b]pyridin-3-one were reacted with 76 mg (0.47 mmol) of 4-methylpiperidine-1-carbonyl chloride. Yield: 29 mg (27%), M+H+: 278.13.

Example 5

Benzo[d]isothiazol-3-yl 4-methylpiperidine-1-carboxylate

In analogy to example 1, 45 mg (0.3 mmol) of benzo[d]isothiazol-3-one were reacted with 58 mg (0.36 mmol) of 4-methylpiperidine-1-carbonyl chloride. Yield: 26 mg (32%), M+H+: 277.14.

Example 6

1-Hexyl-3-(5-nitrobenzo[d]isothiazol-3-yl)urea 100 mg (0.513 mmol) of 5-nitrobenzo[d]isothiazol-3-ylamine were suspended in 5 ml of THF. Addition of 78.1 mg (0.61 mmol) of 1-isocyanatohexane was followed by stirring at RT for 2 h and at 70° C. for 2 h. Then a further 0.3 mmol of 1-isocyanatohexane was added, and stirring was continued at 70° C. for 6 h. The reaction mixture was concentrated, and the residue was dissolved in water and extracted with ethyl acetate. The organic phase was concentrated and purified by preparative HPLC (PR18, acetonitrile/water 0.1% TFA). Yield: 18 mg (11%), M+H+: 323.15.

Example 7

1-(2-Methylbenzyl)-3-(5-nitrobenzo[d]isothiazol-3-yl)urea

In analogy to example 6, 100 mg (0.51 mmol) of 5-nitrobenzo[d]isothiazol-3-ylamine were reacted with 90.4 mg (0.61 mmol) of 1-isocyanatomethyl-2-methylbenzene. Yield: 11 mg (6%), M+H+: 343.16.

Example 8

1-Benzo[d]isoxazol-3-yl-3-hexylurea

In analogy to example 6, 100 mg (0.75 mmol) of benzo[d]isothiazol-3-ylamine were reacted with 114 mg (0.89 mmol) of 1-isocyanatohexane. Yield: 27 mg (14%), M+H+: 262.15.

Example 9

Isothiazolo[5,4-b]pyridine-3-yl 4-trifluoromethylpiperidine-1-carboxylate

In analogy to example 1, 2.99 g (9.82 mmol) of isothiazolo[5,4-b]pyridin-3-ol were reacted with 2.33 g (10.81 mmol) of 4-trifluoromethylpiperidine-1-carbonyl chloride. Yield: 1.3 g (40%), M+H+: 332.09.

Example 10

6-Chloroisoxazolo[5,4-b]pyridin-3-yl 4-methylpiperidine-1-carboxylate

In analogy to example 1, 55 mg (0.32 mmol) of 6-chloroisoxazolo[5,4-b]pyridin-3-ol were reacted with 62.7 mg (0.39 mmol) of 4-methylpiperidine-1-carbonyl chloride. Yield: 22 mg (24%), M+H+: 296.04.

Example 11

6-Methylisoxazolo[5,4-b]pyridin-3-yl 4-methylpiperidine-1-carboxylate

In analogy to example 1, 140 mg (0.93 mmol) of 6-methylisoxazolo[5,4-b]pyridin-3-ol were reacted with 181 mg (1.12 mmol) of 4-methylpiperidine-1-carbonyl chloride. Yield: 135 mg (53%), M+H+: 276.10.

What is claimed is:
1. A compound of the formula I

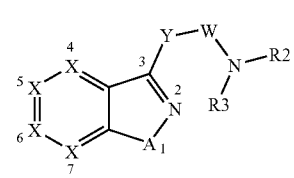

in which:

A is S or O;

W is —(C=O)—, —(S=O)— and —(SO$_2$)—;

X is identically or differently =C(—R)—;

Y is —O— or —NR1-;

R is hydrogen, halogen, ($C_1$-$C_6$)-alkyl, ($C_1$-$C_3$)-alkyloxy-($C_1$-$C_3$)-alkylene, hydroxy, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylamino-carbonyl, COOR4, trifluoromethyl, ($C_1$-$C_6$)-alkylsulfonyl, ($C_1$-$C_6$)-alkylsulfinyl, aminosulfonyl, nitro, pentafluorosulfanyl, ($C_6$-$C_{10}$)-aryl, CO—NR2R3, O—CO—NR2R3, O—CO—($C_1$-$C_6$)-alkylene —CO—O—($C_1$-$C_6$)-alkyl, O—CO—($C_1$-$C_6$)-alkylene-CO—OH, O—CO—($C_1$-$C_6$)-alkylene-CO—NR2R3 or unsubstituted or mono- or poly-F-substituted ($C_1$-$C_6$)-alkyloxy;

R1 is hydrogen, ($C_1$-$C_6$)-alkyl, benzyl;

NR2R3 is piperidine which comprises the atomic member CHR5 in position 4;

R4 is hydrogen, ($C_1$-$C_6$)-alkyl, benzyl;

R5 is ($C_1$-$C_6$)-alkyl, halogen, trifluoromethyl, cyclopropyl, cyclopropylene;

The tautomeric forms of the compound and the physiologically tolerated salts thereof.

2. The compound of formula I as claimed in claim 1, wherein X in position 4 and 5 is =C(—R)— with R=hydrogen, and in position 6 R is not hydrogen.

3. A medicament comprising one or more compounds of formula I as claimed in claim 1.

4. A medicament as claimed in claim 3, which further comprises at least one additional active ingredient selected from antidiabetics, hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients acting on the ATP-dependent potassium channel of the beta cells, CART agonists, NPY agonists, MC4 agonists, orexin antagonists, H3 agonists, TNF agonists, CRF antagonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators, TR-β agonists and amphetamines.

5. A medicament comprising one or more of the compounds of formula I as claimed in claim 1 in admixture with a pharmaceutically suitable carrier in a form suitable for administration.

6. A process for preparing a compound of formula I as claimed in claim 1 which comprises either (1) acylating an azole of formula II with a carbamoyl chloride of formula III; or (2) reacting said azole of formula II in two stages, first with phosgene or an equivalent thereof, such as trichloromethyl chlorocarbonate, ditrichloromethyl carbonate or 4-nitrophenyl chloroformate, and thereafter, in a second step, reacting the resulting product with an amine of formula IV, as summarized in the following scheme, in which the substituents are as defined in claim 1

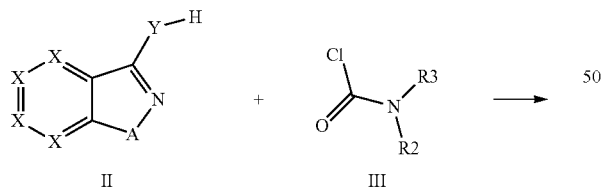

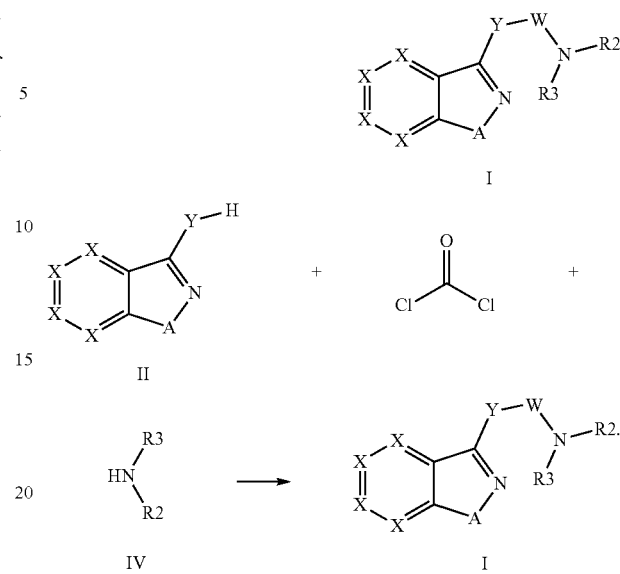

7. A process for preparing a compound of general formula I wherein R3 is hydrogen (formula Ia) as claimed in claim 1, which comprises reacting an azole of formula II with an isocyanate of formula V, O=C=N—R2, as summarized in the following reaction scheme, in which the substituents are as defined in claim 1

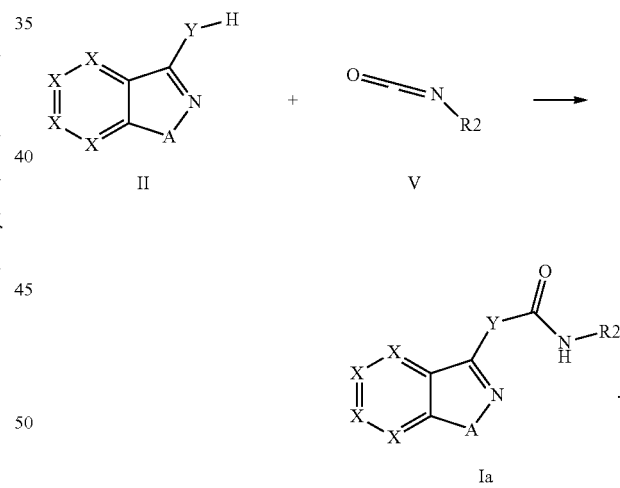

* * * * *